United States Patent [19]

Yamaguchi et al.

[11] Patent Number: 4,927,516

[45] Date of Patent: May 22, 1990

[54] ENZYME SENSOR

[75] Inventors: Shuichiro Yamaguchi, Fuji; Naoto Uchida; Takeshi Shimomura, both of Fujinomiya; Noboru Oyama, Fuchu, all of Japan

[73] Assignee: Terumo Kabushiki Kaisha, Tokyo, Japan

[21] Appl. No.: 65,908

[22] Filed: Jun. 24, 1987

[30] Foreign Application Priority Data

Jun. 27, 1986 [JP] Japan .................. 61-149753

[51] Int. Cl.⁵ .................................... G01N 27/30
[52] U.S. Cl. ..................... 204/403; 204/153.12; 435/288; 435/291; 435/817
[58] Field of Search ............. 204/403, 418, 1 E; 435/817, 291, 288

[56] References Cited

U.S. PATENT DOCUMENTS

| | | | |
|---|---|---|---|
| 4,340,448 | 7/1982 | Schiller et al. | 204/1 T |
| 4,376,689 | 3/1983 | Nakamura et al. | 204/403 |
| 4,655,880 | 4/1987 | Liu | 204/403 |
| 4,671,288 | 6/1987 | Gough | 204/403 |
| 4,680,268 | 7/1987 | Clark | 204/403 |
| 4,704,193 | 11/1987 | Bowers et al. | 204/1 T |

FOREIGN PATENT DOCUMENTS

| | | | |
|---|---|---|---|
| 61-213662 | 9/1986 | Japan . | |
| 240849 | 10/1987 | Japan | 204/403 |
| 1442303 | 7/1976 | United Kingdom . | |

*Primary Examiner*—G. L. Kaplan
*Attorney, Agent, or Firm*—Burns, Doane, Swecker & Mathis

[57] ABSTRACT

Disclosed is an enzyme sensor for measuring a predetermined substrate concentration by potentiometric or amperometric response on the basis of an enzyme. In one aspect, a solid-state enzyme sensor measures a predetermined substrate concentration by potentiometric response and includes a solid enzyme membrane-coated electrically conductive base, redox layer or ion-sensitive layer. In another aspect, a solid-state enzyme sensor measures a predetermined substrate concentration by amperometric response and includes a solid enzyme membrane-coated oxygen reduction catalyst layer. Also disclosed is an enzyme control layer for controlling the outflow and inflow of the enzyme layer.

36 Claims, 6 Drawing Sheets

ENZYME SENSOR

BACKGROUND OF THE INVENTION (1) Field of the Invention

This invention relates to an enzyme sensor and, more particularly, to an enzyme sensor for measuring a substrate concentration by potentiometric or amperometric response on the basis of a molecular identifying function of an enzyme.

(2) Description of the Prior Art

Glucose sensors and urea sensors are known as examples of enzyme sensors utilizing an enzyme reaction. Glucose sensors utilize the following enzyme reaction:

$$\text{glucose} + O_2 + H_2O \xrightarrow{\text{enzyme (glucose oxidase: GOD)}} \text{gluconolactone acid} + H_2O_2$$

According to the principle of the conventional glucose sensor, the concentration of the substrate glucose is measured by measuring the rate of in vivo $O_2$ consumption or the rate of in vivo $H_2O_2$ production using an enzyme sensor. In an enzyme sensor of this kind, however, an enzyme membrane is bonded on a gas-permeable membrane of an oxygen sensor or the like, so that the size of the enzyme sensor depends upon the oxygen sensor. Miniaturizing the enzyme sensor is difficult.

A method is available for measuring glucose concentration by using a pH sensor to detect the amount of change of a hydrogen ion concentration due to the production of gluconic acid, and use of a glass electrode pH sensor and an ion-selective FET sensor has been reported.

When a glass electrode is employed, however, response resulting from deposition of an enzyme layer is very unstable since the resistance of the electrode membrane is very high. Another drawback is the large size of the sensor. Though a reduction in size is possible if the ion-selective FET sensor is used, the adhesion of the enzyme layer presents a problem. Moreover, since a large-scale manufacturing apparatus is required, fabrication is not easy. The same problems are encountered in other enzyme sensors as well.

SUMMARY OF THE INVENTION

An object of the present invention is to provide a solid-state enzyme sensor for measuring the concentration of a substrate potentiometrically, which sensor is adapted to solve the aforementioned problems of the prior art.

Another object of the present invention is to provide a miniature, highly sensitive enzyme sensor for measuring a change in the concentration of a substrate as a change in an amount of current.

A further object of the present invention is to provide an easily fabricated, highly durable, compact enzyme sensor in which the enzyme layer exhibits excellent adhesion.

According to the present invention, the foregoing objects are attained by providing an enzyme sensor for measuring a predetermined substrate concentration on the basis of a molecular identifying function of an enzyme, comprising an electrically conductive base, and an enzyme layer consisting of an enzyme coating the surface of the electrically conductive base for promoting a chemical reaction of the substrate.

In another aspect of the invention, the enzyme sensor comprises an electrically conductive base, a redox layer coating the surface of the electrically conductive base, and an enzyme layer consisting of an enzyme coating the surface of the redox layer for promoting a chemical reaction of the substrate.

In a further aspect of the invention, the enzyme sensor comprises an electrically conductive base, a redox layer coating the surface of the electrically conductive base, an ion-sensitive layer coating the surface of the redox layer for responding to a predetermined ion, and an enzyme layer consisting of an enzyme coating the surface of the ion-sensitive layer for promoting a chemical reaction of the substrate.

Preferred embodiments of the invention are as follows:

1. The enzyme is glucose oxidase for measuring glucose concentration.
2. The enzyme is urease for measuring urea concentration.
3. The enzyme is uricase for measuring uric acid concentration.
4. The enzyme is cholesterol oxidase for measuring cholesterol concentration.
5. The enzyme is imparted with a cross-linked structure by a cross-linking agent.
6. The electrically conductive base is carbon having a graphite structure.
7. The redox layer is selected from a group of substances which undergo a quinone hydroquinone-type oxidation-reduction reaction.
8. The redox layer is selected from a group of substances which undergo an amino quinoid-type oxidation-reduction reaction.
9. The redox layer is selected from a group of substances which undergo a poly(pyrrole), poly (chenilene) oxidation-reduction reaction.

Thus, in accordance with the invention, there is provided a solid-state enzyme sensor for measuring a substrate concentration potentiometrically. There is also provided an enzyme sensor possessing a simple structure and arrangement, so that the sensor is easy to fabricate, has an enzyme layer exhibiting excellent adhesion, is both very stable and highly durable and capable of being readily reduced in size. As a result, by being combined with a catheter, the sensor makes it possible to take measurements in vivo. Further, there is provided an enzyme sensor which has a wide range of linearity between the logarithm of concentration and potential values, and which exhibits a stable response In still another aspect of the invention, there is provided an enzyme sensor comprising an electrically conductive base, an oxygen reduction catalyst layer coating the electrically conductive base, and an enzyme layer containing an enzyme coating the oxygen reduction catalyst layer, wherein the concentration of oxygen consumed by an enzyme reaction is measured by a redox current.

Thus, in accordance with the invention, there is provided a miniature, highly sensitive enzyme sensor for measuring a change in the concentration of a substrate as a change in an amount of current.

More specifically, (1) since membranes are formed by using an electrolytic polymerization process, an electrode having any desired shape can be fabricated, and a miniature enzyme sensor can be manufactured. A multisensor can be manufactured. Furthermore, since the formation of the membranes via polymerization can be performed under comparatively moderate temperature conditions, loss of enzyme activity can be suppressed.

As a result, a high sensitivity can be obtained. (2) Since a current measurement method is used the speed of response is several minutes. This is much quicker in comparison with the potentiometric method, in which the speed of response is several tens of minutes.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

Figure 9:
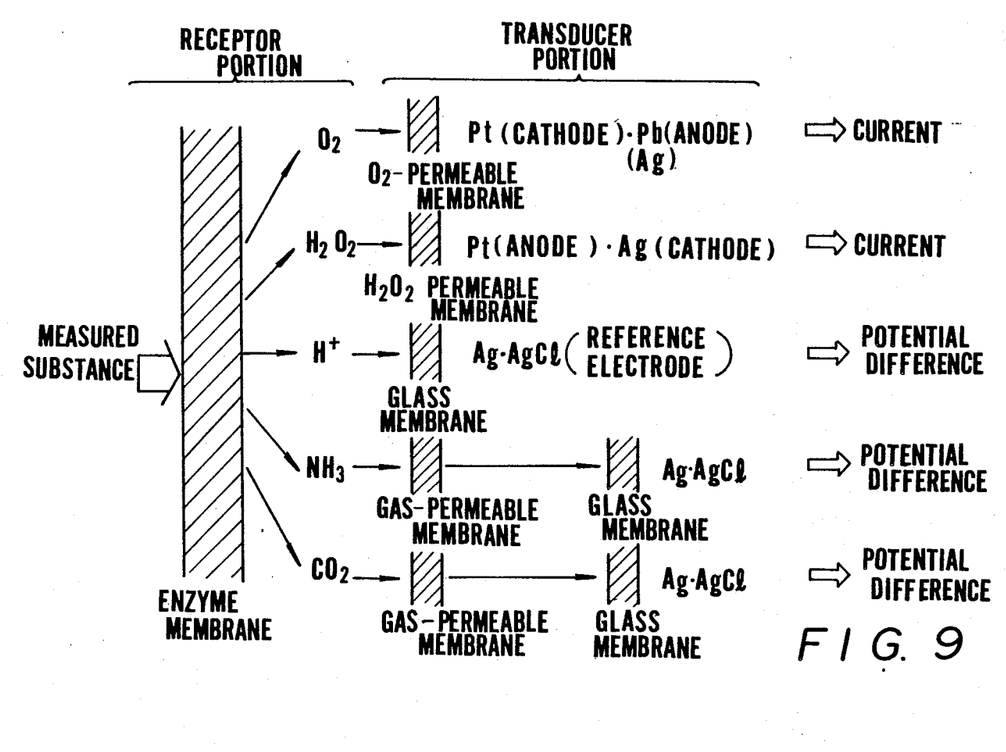
FIG. 9 is a view for describing conventional enzyme sensors.

An enzyme sensor is one of the first biosensors developed and has a transducer portion, which is an electrode at which signal conversion occurs. For this reason, an enzyme sensor is often referred to as an enzyme electrode. An enzyme sensor includes a receptor portion, constituted by an enzyme layer, at which molecular identification occurs. Various layers are used at the transducer portion. FIG. 9 illustrates the basic construction of the principal enzyme sensors. The changes in a substance brought about at an enzyme layer involve $O_2$, $H_2O_2$, $H^+$, $NH_3$, $CO_2$, etc. These substances reach a gas-permeable layer or the like in the transducer portion and are electrochemically converted into electric signals.

In the case of a glucose enzyme sensor, for example, an enzyme layer to which glucose oxidase (GOD) has been fixed is used in the receptor portion. When the receptor portion molecularly identifies glucose, $O_2$ decreases or $H_2O_2$ increases. This is expressed by the following:

In other words, a glucose enzyme sensor can be obtained by intimately affixing a GOD layer to an oxygen-permeable layer or hydrogen peroxide layer of an oxygen electrode or hydrogen peroxide layer.

However, as mentioned above in the description of the prior art, measurement is based on current values and there is a limit on miniaturization due to the use of glass electrodes.

Therefore, in the present embodiment, use is made of the fact that the oxidation reaction of glucose can be broken down into the following two reactions:

and gluconolactone($H^+$) in reaction (1) is measured by a solid-state pH electrode, solid-state electrode or the like.

Combining reactions (1) and (2), we have liquid-interface-(electrode surface)-interface-liquid where $(GOD)_{Ox}$ represents glucose oxidase in the oxidized state and $(GOD)_{Red}$ represents glucose oxidase in the reduced state.

Three types of enzyme sensors, described below, were prepared.

EXAMPLE 1

Figure 1:
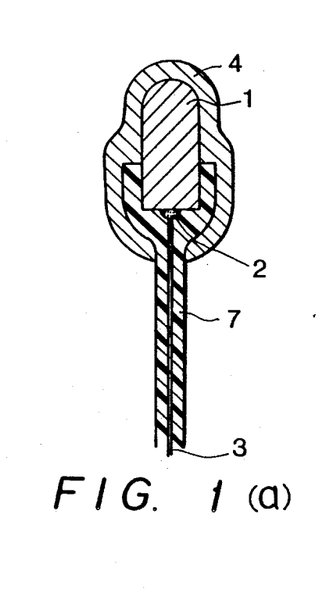
FIG. 1(a) is a schematic view showing the construction of an enzyme sensor of a first embodiment.
FIG. 1(b) is a schematic view showing the construction of an enzyme sensor of a second embodiment.
FIG. 1(c) is a schematic view showing the construction of an enzyme sensor of a third embodiment.

FIG. 1(a) is a schematic view illustrating the construction of an enzyme sensor in accordance with the present embodiment.

(1) Electrically conductive base

A lead wire 3 (copper wire ZUE-CM5W, manufactured by Totoku) was connected by means of an electrically conductive adhesive 2 (C-850-6, Amicon) to the end face of basal plane pyrolytic graphite 1 (diameter 1.0 mm, length 3.5 mm, hereinafter referred to as "BPG" 1). This was followed by coating and insulating the periphery with fluorocarbon polymer (TC-7405, manufactured by Daikin Industries Ltd.) and a Teflon tube 7 (outer diameter: about 1.40 mm). The result was the BPG electrode 1.

(2) Enzyme layer

A glucose oxidase layer 4 was deposited to a thickness of about 1 mm on the surface of the prepared BPG electrode 1. The layer 4 was deposited by a cross-linking process using glutaraldehyde as a cross-linking agent. The cross-linked structure prevents the glucose oxidase from eluting into a liquid specimen.

(Solution A): 15 wt-% bovine serum albumin was dissolved in a pH 8.04 phosphate buffer solution, and 0.5 g of glucose oxidase was dissolved in 5 ml of the resulting solution.

(Solution B): 25% glutaraldehyde aqueous solution (Solution C): 10% glycin aqueous solution The BPG electrode 1 was dipped into Solution A, dried for about 1 min, dipped into Solution B and then dried for 1 min. This procedure was repeated until a layer having a thickness of about 1 mm was formed on the electrode. The electrode was then dipped into Solution C for 1 min, thereby removing unreacted glucose oxidase. Thus completes the deposition of the glucose oxidase layer 4.

FIG. 1(b) is a schematic view illustrating the construction of an enzyme sensor in accordance with the present embodiment.

(1) Electrically conductive base

A BPG electrode 1, identical with that of Example 1, was prepared.

(2) Redox layer

Electrolytic polymerization was carried but under the following conditions using a three-electrode cell in which the prepared BPG electrode, a platinum cell and a silver/silver chloride electrode served as a working electrode, a counter electrode and a reference electrode, respectively, thereby directly depositing a redox layer 5 on the BPG electrode surface:

Composition of electrolyte solution

| | |
|---|---|
| 2,6-dimethylphenol | 0.5 M |
| sodium perchlorate | 0.2 M |

Electrooxidation polymerization conditions

The electrode potential was swept three times (sweep rate: 50 mV/sec) from 0 to +1.5 V (vs. Ag/AgCl), followed by carrying out constant-potential electrolysis for 10 min at +1.5 V. The electrolysis was carried out at $-20°$ C.

(3) Enzyme layer

A glucose oxidase layer 4 was deposited, through a procedure similar to that used in Example 1, on the surface of the redox layer 5 of the electrode.

EXAMPLE 3

FIG. 1(c) is a schematic view illustrating the construction of an enzyme sensor in accordance with the present embodiment.

(1) Electrically conductive base

A BPG electrode 1, identical with that of Example 1, was prepared.

(2) Redox layer

The redox layer 5 was deposited on the surface of the BPG electrode 1 through a process similar to that employed in Example 2.

(3) Ion-sensitive layer

A hydrogen-ion carrier layer 6, the composition of which is shown hereinbelow, was deposited on the surface of the redox layer 5 formed as described above. The hydrogen-ion carrier layer 6 was deposited by repeatedly dipping the BPG electrode 1, having the redox layer 5 deposited thereon, into a tetrahydrofuran mixture, and allowing the same to dry. The dipping and drying steps were repeated 10 times.

Hydrogen-ion carrier composition

| | |
|---|---|
| dioctyl sebacate (DOS) | 15 wt % |
| polyvinyl chloride (PVC, $P_n = 1050$) | 32.7 wt % |
| tridodecyl amine | 4.0 wt % |
| tetrakis(p-chlorophenyl) potassium borate | 0.6 wt % |

(4) Enzyme layer

A glucose oxidase layer 4 was deposited, through a procedure similar to that used in Example 1, on the surface of the hydrogen-ion carrier layer 6.

EXPERIMENT 1

Figure 2:
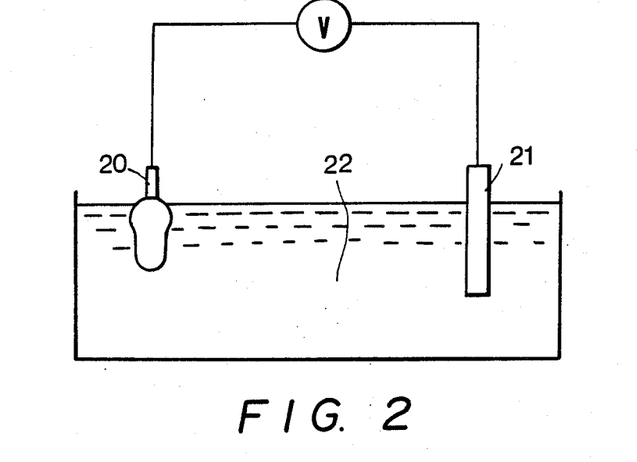
FIG. 2 is a circuit diagram of a measurement circuit using an enzyme sensor of the present embodiment.

As shown in FIG. 2, the glucose concentration of a liquid specimen 22 was subjected to a step-wise change and the response of the enzyme sensors prepared in accordance with Examples 1, 2 and 3 was investigated. This was done by measuring the potential difference across a reference electrode (a saturated sodium chloride calomel electrode) 21 and an enzyme sensor 20 representing those prepared hereinabove. The temperature of the liquid specimen was regulated at 37° C., and the room temperature, i.e. 21° C.–37° C.

Experimental Method

The pH value of the liquid specimen 22 was adjusted to 6.2 by addition of a phosphate buffer solution. A high-concentration aqueous glucose solution (37° C.) was added dropwise to a 37° C. aqueous solution varying the concentration thereof. As this was being done, the potential of the enzyme sensor 20 with respect to the reference electrode 21 was measured. The potential values of the enzyme sensor were measured 10 min after the addition of the glucose solution in order to allow the system to stabilize.

Figure 3:
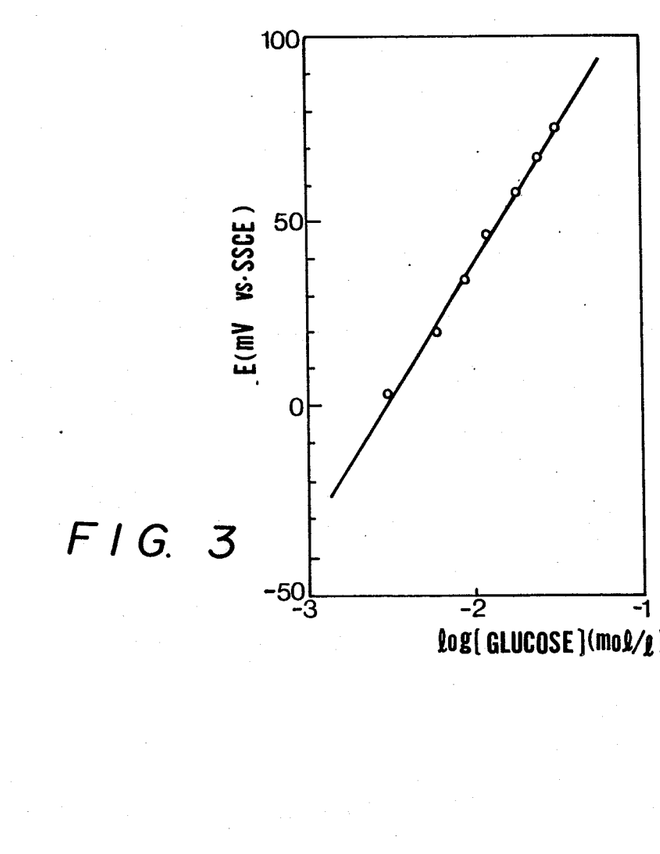
FIG. 3 is a view illustrating the results of a measurement taken with the enzyme sensor of the first embodiment.
Figure 4:
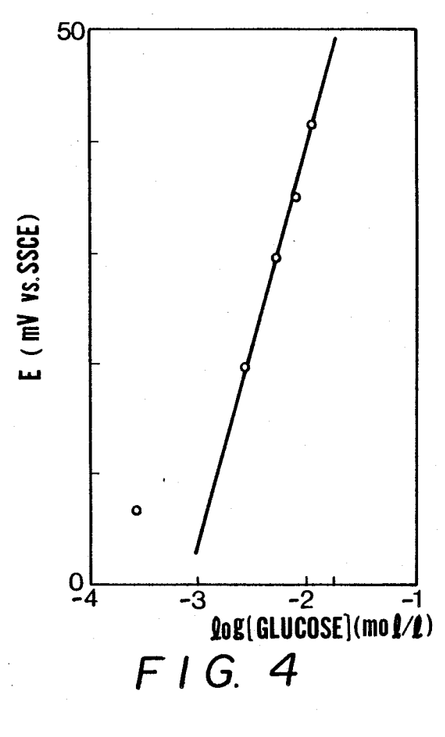
FIG. 4 is a view illustrating the results of a measurement taken with the enzyme sensor of the second embodiment.
Figure 5:
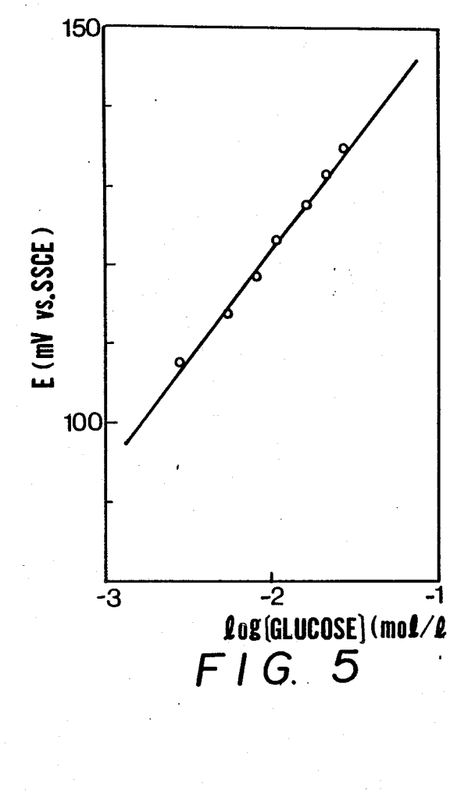
FIG. 5 is a view illustrating the results of a measurement taken with the enzyme sensor of the third embodiment.

The results of measurement are as shown in FIGS. 3 through 5, in which the glucose concentration is shown as a molar concentration, namely the mole number of glucose in 1 liter of the liquid specimen. These graphs show excellent linearity between the logarithm of glucose concentration and the potential response of the enzyme sensors.

The approximate expressions for the respective Examples are as follows:

Enzyme sensor of Example 1:

| | |
|---|---|
| Enzyme sensor of Example 1: <br> E = 191.9 + 74.8 log (glucose) (mol/l) | from FIG. 3 |
| Enzyme sensor of Example 2: <br> E = 190.7 + 38.7 log (glucose) (mol/l) | from FIG. 4 |
| Enzyme sensor of Example 3: <br> E = 176.8 + 27.6 log (glucose) (mol/l) | from FIG. 5 |

In the present embodiment, glucose concentration was measured by depositing the glucose oxidase layer. However, similar results were obtained with regard to enzyme sensors using other enzymes. For example, urea concentration was measured using a urease layer, uric acid concentration using a uricase layer, and cholesterol concentration using a cholesterol oxidase layer. Further, the structural requisites of the present invention are an enzyme for inducing a predetermined reaction in a substrate, and a solid-state ion sensor, which is devoid of an internal liquid chamber, for measuring the change in ion concentration caused by the ions generated. The invention is not limited to measurement of hydrogen ion described in the above examples, and solid-state ion sensors can be constructed for measuring other ions. The technical concept of the invention can be broadened to cover other ion sensors such as bacteria sensors, immunological sensors and the like.

EXPERIMENT 4

Figure 6A:
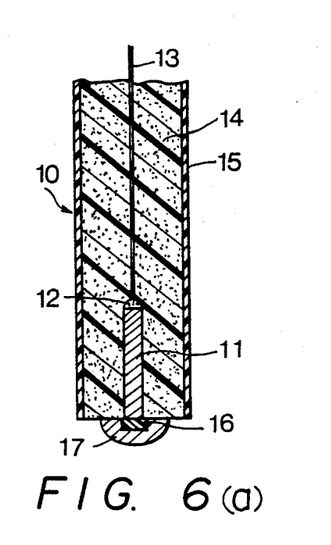
FIG. 6(a) is a schematic view of a glucose sensor fabricated in accordance with a fourth embodiment.

FIG. 6(a) is a schematic view illustrating the structure of a glucose sensor formed in accordance with the present embodiment. The method of preparation will now be described.

(1) Preparation of carbon fiber electrode

A cluster of carbon fibers 11 (Carborone, manufactured by Nihon Carbon) was cut to a length of 2.0 cm and a lead wire 13 was connected to one terminus of the fibers by an electrically conductive adhesive 12 (Cyclone B, manufactured by Amicon). The periphery of the electrode was covered and insulated by an expoxy-type bonding agent 14 and a Teflon tube 15. Only the cross section 11a of the carbon fibers was employed as the electrode surface. The electrode surface area was $1.2 \times 10^{-4}$ cm$^2$.

(2) Application of cobalt porphyrin membrane

An electrolytic polymerization membrane 16 of meso-tetra(o-aminophenyl) cobalt porphyrin was deposited under the following conditions using a three-electrode cell in which the carbon fiber electrode prepared in (1), a platinum coil and a silver/silver chloride electrode served as a working electrode, a counter electrode and a reference electrode, respectively:

Composition of electrolyte solution

| meso-tetra(o-aminophenyl) cobalt porphyrin | 20 mmol/l |
|---|---|
| sodium perchlorate | 0.1 mol/l |
| acetonitrile | solvent |

The electrode potential was swept three times (sweep rate: 50 mV/sec) from 0 to +1.8 V (vs. Ag/AgCl), followed by carrying out constant-potential electrolysis for 30 min at +1.8 V, thereby completing the deposition of the membrane.

(3) Enzyme layer

A glucose oxidase membrane was deposited through the following process using a three-electrode cell in which the carbon fiber electrode coated with the cobalt porphyrin membrane prepared in (2), a platinum coil and a silver/silver chloride electrode served as a working electrode, a counter electrode and a reference electrode, respectively:

Composition of electrolyte solution

| 1,2-diaminobenzene | 20 mmol/l |
|---|---|
| glucose oxidase | 50 mg/ml |

The electrode potential was swept three times (sweep rate: 50 mV/sec) from 0 to +1.5 V (vs. Ag/AgCl) in the above mentioned electrolyte solution under nitrogen gas at room temperature, followed by carrying out constant-potential electrolysis for 30 min at +1.5 V (vs. Ag/AgCl) to deposit an enzyme layer 17, thereby forming a completed glucose sensor 10.

EXPERIMENT 2

The following experiment was carried out using the glucose sensor 10 prepared in accordance with Example 4:

A 5 mM phosphate buffer solution of pH 6.20 containing glucose of a known concentration was introduced into an electrolytic cell and the solution served as a liquid specimen. The glucose sensor 10 prepared in accordance with Example 4 and at Ag/AgCl electrode were inserted into the liquid specimen. The potential of the glucose sensor 10 was made −0.5 V with respect to an Ag/AgCl electrode, and the value of a current across the glucose sensor 10 and Ag/AgCl electrode was measured at such time. The glucose concentration in the liquid specimen was then varied and the current was measured in the same manner.

The glucose concentration in the liquid specimen was varied through the following method: In the first measurement, the specimen was made a dilute solution (30 mg/dl). From the second measurement onward, the concentration of the specimen was raised by adding a high-concentration solution (1000 mg/dl) dropwise, in a fixed amount, to the specimen. Measurements were taken at a temperature of 32°±0.1° C., and current values were recorded about 2 min after the start of measurement to assure that the values were stable.

Figure 7:
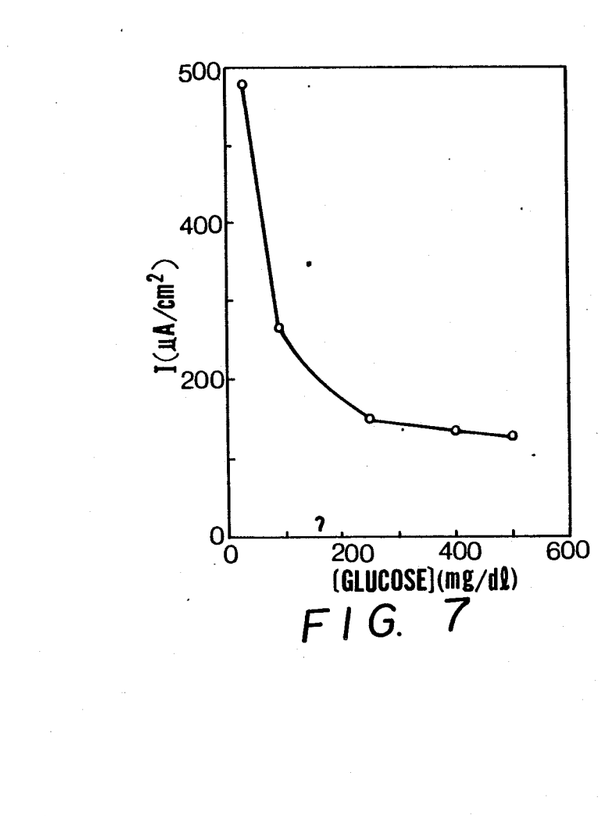
FIG. 7 is a graph showing the relationship between glucose concentration and current density using the glucose sensor of the fourth embodiment.

The glucose concentrations and current values obtained as the results of measurement are shown in Table 1, and a plot of the values is illustrated in FIG. 7. It will be appreciated that the current values decrease as the glucose concentration rises. Accordingly, it will be understood that the glucose concentration of the liquid specimen can be estimated from the observed current values by drawing a calibration curve.

EXAMPLE 5

Figure 6B:
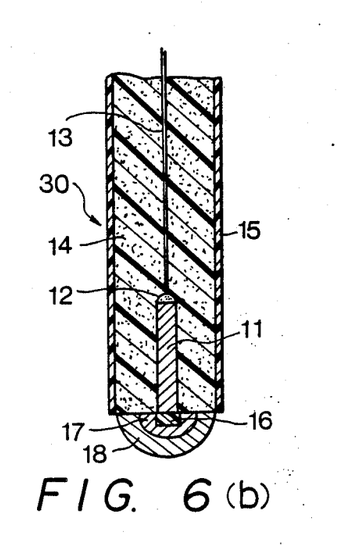
FIG. 6(b) is a schematic view of a glucose sensor fabricated in accordance with a fifth embodiment.

FIG. 6(b) is a schematic view illustrating the structure of a glucose sensor 30 formed in accordance with the present embodiment. The method of preparation will now be described.

(1)–(3) Preparation of glucose sensor

By using a process similar to that employed in Example 4, a glucose sensor was formed by preparing a carbon fiber electrode, coating the electrode with the cobalt porphyrin membrane 16, and coating the resulting body with the enzyme membrane 17.

(4) Application of cellulose acetate membrane

Next, the glucose sensor 30 was formed by coating the coated electrode with a cellulose acetate membrane 18 and controlling the enzyme outflow and the arrival of the substrate (glucose) at the electrode when a measurement is taken. The application of the cellulose acetate membrane 18 was performed by a dipping method using a dichloromethane solution of 10% cellulose acetate as a dipping solution.

EXPERIMENT 3

Figure 8:
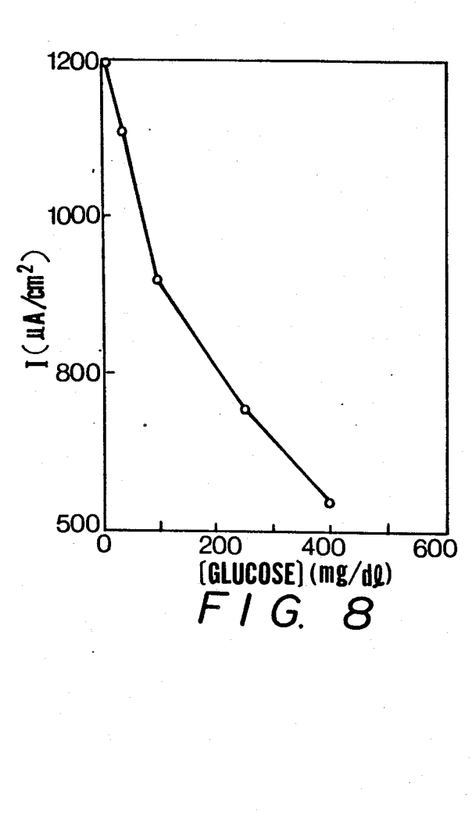
FIG. 8 is a graph showing the relationship between glucose concentration and current density using the glucose sensor of the fifth embodiment.

Measurements similar to those of Experiment 2 were taken using the glucose sensor 30 prepared in accordance with Example 5. The values obtained are shown in Table 2, and a plot of the results is shown in FIG. 8. In comparison with the glucose sensor 10 of Example 4, better linearity is obtained between glucose concentration and the current values, and sensitivity is improved. Thus, an improved glucose sensor could be provided.

Though an embodiment has been described in which the invention is applied to a glucose sensor, the technical concept of the invention can be applied to other enzyme sensors and to such biosensors as bacteria sensors.

The enzyme sensor of the present invention has the following advantages:

(1) Since membranes are formed by using an electrolytic polymerization process, an electrode having any desired shape can be fabricated, and a miniature enzyme sensor can be manufactured. A multisensor can be manufactured. Furthermore, since the formation of the membranes via polymerization can be performed under comparatively moderate temperature conditions, loss of enzyme activity can be suppressed. As a result, a high sensitivity can be obtained.

(2) Since a current measurement method is used, the speed response is several minutes. This is much quicker in comparison with the potentiometric method, in which the speed of response is several tens of minutes.

What is claimed is:

1. An enzyme sensor for measuring a substrate concentration using an enzyme, comprising:
   an electrically conductive carbon having a graphite structure for generating an electric potential responsive to a hydrogen ion concentration;
   an enzyme layer comprising an enzyme imparted with a cross-linked structure by a cross-linking agent coating a surface of said electrically conductive carbon having a graphite structure, said enzyme layer being capable of generating a change in said hydrogen ion concentration by promoting the chemical reaction of a substrate on which said enzyme is active; and
   measuring means for measuring the electric potential of said electrically conductive carbon having a graphite structure.

2. The enzyme sensor according to claim 1, wherein said enzyme is glucose oxidase for measuring glucose concentration.

3. The enzyme sensor according to claim 1, wherein said enzyme is urease for measuring urea concentration.

4. The enzyme sensor according to claim 1, wherein said enzyme is uricase for measuring uric acid concentration.

5. The enzyme sensor according to claim 1, wherein said enzyme is cholesterol oxidase for measuring cholesterol concentration.

6. The enzyme sensor according to claim 1, further comprising a cellulose acetate layer coating a surface of said enzyme layer.

7. The enzyme sensor according to claim 6, wherein the enzyme layer comprises the enzyme fixed to an oxygen reduction catalyst layer by electrolytic polymerization.

8. An enzyme sensor for measuring a substrate concentration using enzyme, comprising:
   an electrode generating an electric potential responsive to a hydrogen ion concentration, which electrode comprises an electrically conductive base and an electrolytically polymerized redox layer coating a surface of said electrically conductive base and having a redox reaction which is selected from a quinone-hydroquinone type redox reaction, an amine-quinoid type redox reaction and a poly(pyrrole), poly(chenilene) redox reaction and
   an enzyme layer comprising an enzyme and coating a surface of said electrode, said enzyme layer being capable of generating a change in said hydrogen ion concentration by promoting the chemical reaction of a substrate on which said enzyme is active.

9. The enzyme sensor according to claim 8, wherein said enzyme is glucose oxidase for measuring glucose concentration.

10. The enzyme sensor according to claim 8, wherein said enzyme is urease for measuring urea concentration.

11. The enzyme sensor according to claim 8, wherein said enzyme is uricase for measuring uric acid concentration.

12. The enzyme sensor according to claim 8, wherein said enzyme is cholesterol oxidase for measuring cholesterol concentration.

13. The enzyme sensor according to claim 8, wherein said enzyme is imparted with a cross-linked structure by a cross-linking agent.

14. The enzyme sensor according to claim 8, wherein said electrically conductive base is carbon having a graphite structure.

15. An enzyme sensor for measuring a substrate concentration using enzyme, comprising:
   an electrode generating an electric potential responsive to a hydrogen ion concentration, which electrode comprises an electrically conductive base and an electrolytically polymerized redox layer coating a surface of said electrically conductive base wherein said redox layer is selected from a group of substances having a poly(pyrrole), poly(chenilene) oxidation-reduction function.

16. The enzyme sensor according to claim 15, wherein said enzyme is glucose oxidase for measuring glucose concentration.

17. The enzyme sensor according to claim 15, wherein said enzyme is urease for measuring urea concentration.

18. The enzyme sensor according to claim 15, wherein said enzyme is uricase for measuring uric acid concentration.

19. An enzyme sensor for measuring a substrate concentration on the basis of a molecular identifying function of an enzyme, comprising:
   an electrode generating an electric potential responsive to a hydrogen ion concentration, which electrode comprises an electrically conductive base, an electrolytically polymerized redox layer coating a surface of said electrically conductive base, and a hydrogen ion-sensitive layer coating a surface of said redox layer; and
   an enzyme layer comprising an enzyme and coating a surface of said electrode, said enzyme layer being capable of generating a change in said hydrogen ion concentration by promoting the chemical reaction of a substrate on which said enzyme is active.

20. The enzyme sensor according to claim 19, wherein said enzyme is glucose oxidase form measuring glucose concentration 21. The enzyme sensor according to claim 19, wherein said enzyme is urease for measuring urea concentration.

22. The enzyme sensor according to claim 19, wherein said enzyme is uricase for measuring uric acid concentration.

23. The enzyme sensor according to claim 19, wherein said enzyme is cholesterol oxidase for measuring cholesterol concentration.

24. The enzyme sensor according to claim 19, wherein said enzyme is imparted with a cross-linked structure by a cross-linking agent.

25. The enzyme sensor according to claim 19, wherein said electrically conductive base is carbon having a graphite structure.

26. The enzyme sensor according to claim 19, wherein said redox layer is selected from a group of substances having a quinone-hydroquinone type redox reaction.

27. The enzyme sensor according to claim 19, wherein said redox layer is selected from a group of substances having an amine-quinoid type redox reaction.

28. The enzyme sensor according to claim 19, wherein said redox layer is selected from a group of substances having a poly(pyrrole), poly(chenilene) oxidation-reduction function.

29. An enzyme sensor for measuring a substrate concentration on the basis of a molecular identifying function of an enzyme, comprising:
   an electrically conductive base;
   an oxygen reduction catalyst layer being electrolytically polymerized from an electrolyte solution containing a phthalocyanine or a porphyrin complex coating said electrically conductive base; and
   an enzyme layer containing an enzyme and electrolytically coating said oxygen reduction catalyst layer.

30. The enzyme sensor according to claim 29, wherein the enzyme layer comprises the enzyme fixed to the oxygen reduction catalyst layer by electrolytic polymerization.

31. The enzyme sensor according to claim 30, wherein said enzyme is glucose oxidase for measuring glucose concentration.

32. The enzyme sensor according to claim 30, wherein said enzyme is urease for measuring urea concentration.

33. The enzyme sensor according to claim 30, wherein said enzyme is uricase for measuring uric acid concentration.

34. The enzyme sensor according to claim 30, wherein said enzyme is cholesterol oxidase for measuring cholesterol concentrate.

35. The enzyme sensor according to claim 30, wherein said enzyme is imparted with a cross-linked structure by a cross-linking agent.

36. The enzyme sensor according to claim 29, wherein said electrically conductive base is selected from the group consisting of carbon fiber, graphite, platinum and gold.

* * * * *